United States Patent
Wade et al.

(10) Patent No.: US 6,383,130 B1
(45) Date of Patent: May 7, 2002

(54) LAP WEIGHT

(76) Inventors: Tana Wade, 10030 Pine Springs Dr., Conroe, TX (US) 77304; Lucia Cook Queen, 16 Thunder Hollow Pl., The Woodlands, TX (US) 77381

( * ) Notice: Subject to any disclaimer, the term of this patent is extended or adjusted under 35 U.S.C. 154(b) by 31 days.

(21) Appl. No.: 09/633,679

(22) Filed: Aug. 7, 2000

(51) Int. Cl.$^7$ .............................................. A61M 21/00
(52) U.S. Cl. ......................................................... 600/27
(58) Field of Search ........................ 600/27, 26; 482/50, 482/105; 434/433, 260, 395; 273/DIG. 30; 2/48, 244

(56) References Cited

U.S. PATENT DOCUMENTS 5,581,833 A * 12/1996 Zenoff ............................ 5/655

OTHER PUBLICATIONS

Velvasoft Weighted Lap Pad, http://www.world-net.net/home/mwsales/LapPad.html, pp. 1–2.*

* cited by examiner

*Primary Examiner*—Kevin Shaver
*Assistant Examiner*—Brian Szmal

(57) ABSTRACT

The lapweight is a weighted pad to be placed across the lap of a seated child who has a sensory processing disorder. The application of deep pressure helps to meet a need for additional sensory stimulation, with the end result of calming and focusing the child. The lapweight is comprised of a machine-washable outer casing whose fabric provides texture for tactile stimulation; four hand-washable fabric inner pouches containing the weighted material, polypropylene pellets; or, as an alternative, four soft pliable plastic inner pouches containing water, with a valve to adjust the amount of water to meet individual weight needs or for ease of transport; and attachable/detachable straps for tying lapweight securely around a child's waist.

4 Claims, 1 Drawing Sheet

FIG. 1
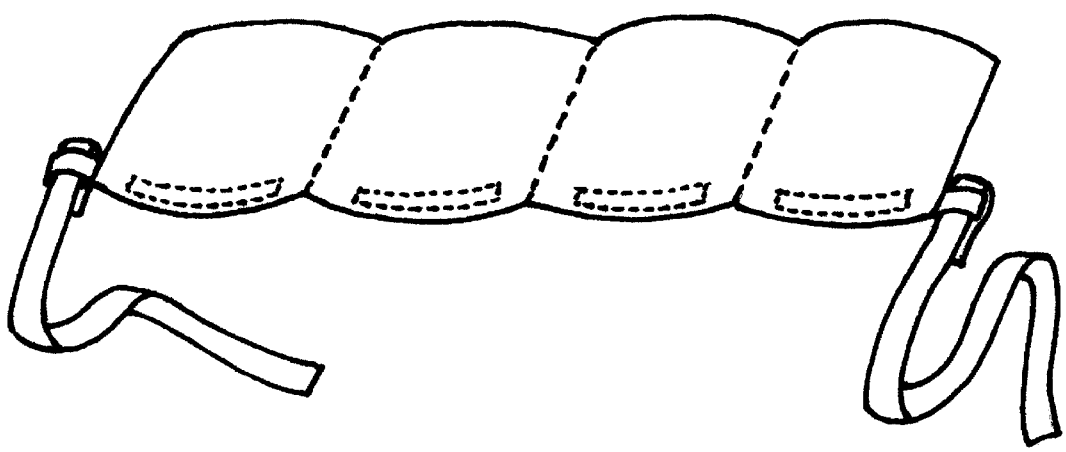
FIG. 2
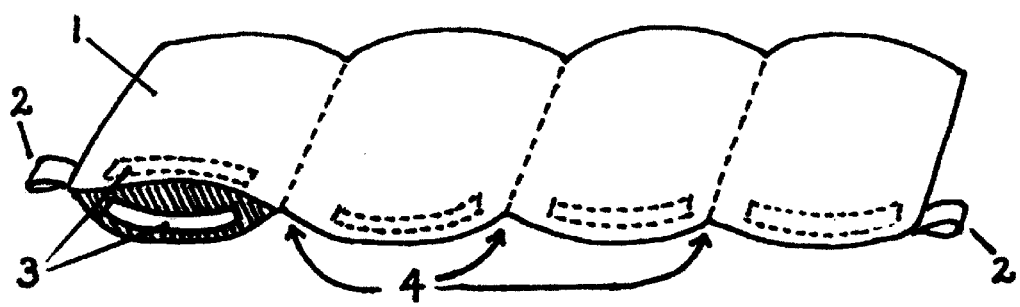
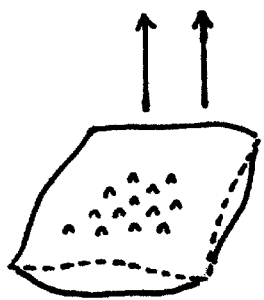
FIG. 3
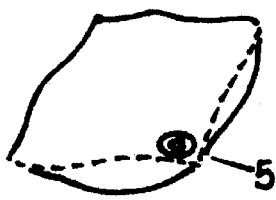
FIG. 4
FIG. 5

LAP WEIGHT

CROSS-REFERENCE TO RELATED APPLICATIONS

Not applicable

STATEMENT REGARDING FEDERALLY SPONSORED RESEARCH OR DEVELOPMENT applicable

REFERENCE TO A MICROFICHE APPENDIX

Not applicable

BACKGROUND OF THE INVENTION

The field of the invention pertains generally to wearing apparel, and particularly to weighted accessories which are worn/positioned on the body to increase sensory stimulation for persons with sensory processing dysfunction. Such accessories are generally used at the direction of an occupational or physical therapist.

Using weight to apply deep pressure to the body is known to satisfy a sensory craving in many persons with autism and other disorders which affect sensory processing, with the end result of calming and focusing the individual. The senses which especially benefit from this type of stimulation are those of body position (proprioception), touch (tactile), and balance (vestibular). When stimuli received from the environment cannot be controlled or integrated by the nervous system, there are frequently resulting behaviors which interfere with attention and learning. Therefore, in any setting where attention to task is required (particularly in an educational setting), a means of satisfying this need is very desirable.

Products currently on the market related to this field of invention are limited, as are publications and documented research on the topic of sensory integration. (Documentation includes books by Temple Grandin, PhD., research by Dr. A. Jean Ayres, and articles in occupational/physical therapy publications.) Known products attempting to meet this particular sensory need include weighted vests and weights worn around the wrists/ankles. However, when used in an educational setting, these products have several disadvantages: their therapeutic appearance sets the students apart from their peers; and the devices used to fasten them (buckles and hook-and-loop fasteners) frequently become a focus of sensory self-stimulation for the child, negating the original intent of calming and focusing the student's attention on a desired task.

Therefore, a need exists for a device which will satisfy a child's craving for additional sensory input in the form of deep pressure, a device that can be conveniently transported and used across settings (school, home, therapy sessions, riding in car, etc.) without further distinquishing him from his peers and without increasing self-stimulatory behaviors. Of additional benefit would be a means of providing for tactile stimulation of a calming nature (that would not distract the child's attention from a directed task) and a means of tying the device around the child's waist if a more secure feeling was desired. The device should be easily cleanable for use by a child, and easily positioned on the body so that the child could regulate the additional sensory input independently as desired.

BRIEF SUMMARY OF THE INVENTION

The present invention is a weighted pad, designed to be placed across the lap of a seated child whose dysfunctional sensory system requires additional stimulation. Pressure provided by the lapweight to the muscles and joints, as well as tactile input available from the texture of the lapweight's fabric, helps to satisfy a basic sensory need, thereby calming the child who is then better able to focus attention on a desired activity.

It is the objective of the invention to provide a weighted lap pad which will serve as a pleasant, unobtrusive, and self-regulating means of calming children with developmental/sensory disorders such as autism, thereby allowing them to focus their attention, instead, on a desired activity. The lapweight is self-regulating in that a child who craves the sensory stimulation of deep pressure can secure comfort from the lapweight independently whenever needed, and can use it for the duration of the seated activity.

It is also an objective of the invention to deliver the desired sensory stimulation in a manner which does not call undue attention to the child's differences from his peers. Products currently on the market to address this need, particularly vinyl vests and wrist/ankle weights, have a therapeutic appearance which is undesirable to older children. The lapweight can be kept in the therapy room or at the child's classroom desk, etc., to be placed across the lap whenever needed.

An important objective of the lapweight is to deliver the desired sensory stimulation without the addition of distracting stimuli. Many children with sensory processing problems have difficulty attending to a requested task; furthermore, it is not uncommon for them to attempt to satisfy sensory needs by manipulating or mouthing objects repetitively. Products currently on the market to meet these sensory needs employ straps, buckles, or hook-and-loop fasteners, any of which can become the object of the child's stimulatory attention. The present invention contains no distracting fastening apparatus positioned within the visual field of the child.

It is a further objective to provide a weighted lap pad with a casing fabric of such texture as to give needed tactile stimulation when stroked, thereby having a calming effect.

Objectives of the present invention also include: serving as a reminder for the child to remain seated, by means of its placement across the lap; and providing a visual reminder that the child's hands should remain down during worktime, with the option of having handprints painted on one side of the lapweight.

Yet another objective of the invention is to offer a weighted lap pad with options as to the manner in which weight is delivered to the device, allowing the customer to vary the amount of weight to meet individual needs, as well as allowing for lighter transport and shipping.

It is an objective of the invention to provide a weighted lap pad with a machine-washable outer casing and with hand-washable inner pouches containing the weighted material.

A further objective of this invention is to provide a weighted lap pad with a means of being tied around the waist of a seated child, if a more secure feeling is desired.

Yet another objective of the invention is to offer a weighted lap pad with custom sizing, weight, and fabric textures to satisfy individual needs.

BRIEF DESCRIPTION OF THE SEVERAL VIEWS OF THE DRAWING

FIG. 1 shows the lapweight with detachable straps attached.

FIG. 2 shows the lapweight's fabric casing, with four sections separated by seams, one section open to show hook-and-loop closure. The view also shows a small loop at each end of lapweight, to attach optional straps for securing lapweight around a child's waist.

FIG. 3 shows a fabric pouch filled with polypropylene pellets, one of four which are inserted into the four sections of the lapweight. Small tents on said fabric pouch represent the apparent texture of the pellets under a light-weight fabric.

FIG. 4 shows an alternate pouch: a butt-seamed plastic bladder with valve, filled with water; one of four which may be inserted into the four sections of the lapweight in place of the fabric pouches.

FIG. 5 shows one of two identical webbing straps with a hook-and-loop fastener at one end, to thread through loops at each end of lapweight, pressing hook and loop together to affix, then tie around a child's waist.

Broken lines shown throughout the views are understood to represent stitching.

DETAILED DESCRIPTION OF THE INVENTION

Referring to FIGS. 1, 2, 3, 4, and 5, an embodiment of the lapweight is shown. In this embodiment several outstanding features are illustrated: casing 1 made of machine washable/dryable fabric selected particularly to provide tactile stimulation (fake fur, brushed denim, corduroy, or the like); webbing loops 2 sewn into end seams, to allow option of attaching straps; pouch options of lightweight fabric filled with polypropylene pellets (shown in FIG. 3) or soft pliable plastic with valve (shown in FIG. 4), to be filled with water; webbing straps with hook-and-loop fasteners at one end 6, to thread through loops 2 and secure lapweight around waist.

FIG. 1 illustrates the embodiment of the invention in its complete form, with weighted pouches in each sealed section of the casing and with the detachable straps attached to secure the lapweight around the waist. When positioned across a seated child's lap, said lapweight is of sufficient length that the two center sections generally cover the lap, leaving two end sections to drape over the sides of the upper legs, providing additional comfort. When positioned properly, the opening edge of the lapweight lies against the waist/stomach.

In FIG. 2 the lapweight casing is illustrated with machine-sewn seams along ends and across back side. A four-inch piece of strong webbing type material is doubled into a loop and sewn into the seam at each end of the casing, adjacent to the open side. Said loop is sewn with its closed end inside casing, so that when casing is turned right side out the closed loop extends out from the end 2, forming a place to affix optional straps (shown in FIGS. 1 and 5). With casing turned right side out, and fabric edges along the open side turned in to create a finished appearance, three seams 4 are sewn from side to side, dividing the casing into four equal sections. Strips of hook-and-loop fastener 3 are then machine-sewn inside the opening of each of the four casing sections, placing hook pieces on one side of each opening and loop pieces on the opposite side, so that when the weighted pouches are inserted into each section the two sides of the openings can be pressed together, forming a seal to keep the pouches in place. FIG. 2 shows one of the four sections open.

The casings, as shown in FIGS. 1 and 2, are constructed from a variety of machine washable/dryable fabrics, chosen specifically for their texture, with some casings combining a different textured fabric on each side. Sensory input obtained from stroking a soft fabric such as fake fur can have a calming effect, much as stroking a pet cat or dog; a rougher texture, providing greater stimulation, may also satisfy a tactile need.

Furthermore, said casings are constructed in a variety of colors, allowing for visual preference. The standard casings are devoid of pattern or ornamentation, reducing visual stimulation which would draw the child's attention away from a designated task; however, an option not shown in this drawing provides for a set of child's handprints to be painted on the two center sections of the top side of the casing. These serve as a visual reminder to the child that hands are to remain down during worktime.

FIG. 3 shows an embodiment of one of four weighted pouches, as it would be inserted into a section of the lapweight casing. The hand-washable pouch is machine-sewn of a light weight fabric. With three sides seamed and turned right side out, commercially available polypropylene pellets are poured into the opening, which is then sewn shut. A uniform amount of pellets is placed in each of the four pouches, distributing the weight evenly over the length of the lapweight. (A standard lapweight contains a total weight of five pounds, with each pouch containing one and one-fourth pounds of pellets. However, it is an option of this invention to be produced in a custom size/weight to meet individual needs.)

FIG. 4 embodies an alternate means of delivering weight to the invention. The soft, pliable pouch is a butt-seamed plastic bladder to be filled with water and emptied by means of a valve 5. One plastic water-filled pouch is inserted into each of the four lapweight casing sections. The plastic water-filled pouch has several advantages over the fabric pellet-filled embodiment, including ease of changing the amount of water, and therefore weight, in the lapweight to satisfy individual need; and convenience when traveling, to lighten packing by draining water out. Beyond that, each type of pouch creates a different feel in the lapweight, to satisfy individual preference.

Referring to FIG. 5, the invention offers the ability to attach straps to the lapweight for the purpose of securing it around the waist of a seated child. The straps are constructed of strong webbing material, durable yet pliable for tying. Each has a square of hook-and-loop fastener 6 positioned at one end, three inches apart, so that when said end of strap is threaded through loop 2, located at each end of the lapweight casing, the strap can be folded over the loop and affixed to itself, thereby attaching the strap to the lapweight. For some children with a sensory processing disorder, the straps serve only as objects for manipulation and are a distraction; for others, the lapweight needs to be cinched tightly to provide adequate stimulation; thus, the option of straps. When the lapweight is positioned across a child's lap, the end loops 2 effectively fall out of the range of vision, and do not serve as a distraction to the child.

While a preferred embodiment of the invention has been described using specific terms, such description is for illustrative purposes only. It is to be understood that changes and variations may be made without departing from the spirit and scope of the following claims.

What is claimed is:

1. A weighted pad, positioned across a lap of a seated child to provide sensory stimulation when said child requires additional sensory input to calm and focus, said weighted pad comprising:

a. a textile outer casing of a rectangular shape, divided into four equal sections by seams, one long side of said casing remaining unseamed with hook-and-loop fasteners to seal each said section;

b. said outer casing is further comprising a machine washable/dryable fabric, of particular textures that satisfy said child's need for tactile stimulation upon stroking;

c. said outer casing is further comprising two webbing end loops, one attached to each end of said casing adjacent to said unseamed side, for the purpose of affixing webbed fabric straps; and d. said webbed fabric straps are removably attached to each said end loops on said outer casing, adapted for securing said weighted pad around a child's waist.

2. The weighted pad according to claim 1 further comprising a set of four hand-washable fabric pouches weighted with polypropylene pellets, to be inserted into each said casing section.

3. The weighted pad according to claim 1 further comprising a set of four soft, pliable plastic pouches weighted with water, to be inserted into each said casing section.

4. The weighted pad according to claim 3, further comprising valves for the intake and release of water, to vary water weight amounts.

* * * * *